(12) United States Patent
Casset

(10) Patent No.: US 7,792,582 B2  
(45) Date of Patent: Sep. 7, 2010

(54) ACTIVE IMPLANTABLE MEDICAL DEVICES, NOTABLY FOR PACING, RESYNCHRONIZATION, DEFIBRILLATION AND/OR CARDIOVERSION, HAVING IMPROVED DIAGNOSIS OF THE PATIENT'S CLINICAL STATUS

(75) Inventor: Cyrille Casset, Paris (FR)

(73) Assignee: ELA Medical S.A.S., Montrouge (FR)

( * ) Notice: Subject to any disclaimer, the term of this patent is extended or adjusted under 35 U.S.C. 154(b) by 860 days.

(21) Appl. No.: 11/563,123

(22) Filed: Nov. 24, 2006

(65) Prior Publication Data

US 2007/0150016 A1 Jun. 28, 2007

(30) Foreign Application Priority Data

Nov. 23, 2005 (FR) .................................. 05 11848

(51) Int. Cl.  
*A61N 1/365* (2006.01)

(52) U.S. Cl. .................................. 607/19; 607/5; 607/9

(58) Field of Classification Search ................. 607/5, 607/9, 19  
See application file for complete search history.

(56) References Cited

U.S. PATENT DOCUMENTS

| 5,766,228 | A | | 6/1998 | Bonnet | |
|---|---|---|---|---|---|
| 6,055,454 | A | * | 4/2000 | Heemels | ..................... 607/19 |
| 6,246,910 | B1 | | 6/2001 | Bonnet | |
| 6,773,404 | B2 | | 8/2004 | Poezevera et al. | |
| 2004/0181260 | A1 | * | 9/2004 | Anderson et al. | ............. 607/17 |

FOREIGN PATENT DOCUMENTS

| EP | 0770407 | 5/1997 |
|---|---|---|
| EP | 0966987 | 12/1999 |
| EP | 1317943 | 6/2003 |

* cited by examiner

*Primary Examiner*—Scott M Getzow  
*Assistant Examiner*—Joseph M Dietrich  
(74) *Attorney, Agent, or Firm*—Orrick Herrington & Sutcliffe, LLP

(57) ABSTRACT

An active implantable medical device, preferably a device for pacing, resynchronization, defibrillation and/or cardioversion of a patient, that includes functionality that assists in the diagnosis of the patient's clinical status. This devices comprises circuits (10, 12) for measuring one physiologic parameter, preferably minute ventilation (VE), and circuits (14, 16) for measuring a physical parameter, preferably acceleration (G), control logic (18) for discriminating between activity and rest phases of the patient, and analysis circuits (20-28), to process and combine these signals and memorize (store in memory) the obtained results in the form of a data history. The analysis will establish characteristics providing, for successive dates, representative values, for a given period of time, of the physical signal and physiologic signal during activity phases of the patient, and/or of the physiologic signal during rest phases. These circuits search for remarkable dates for each of the characteristics and allocate specific indices of clinical status respective to each of the periods comprised between the remarkable dates, then combined the specific thus obtained into one single composite index.

12 Claims, 4 Drawing Sheets

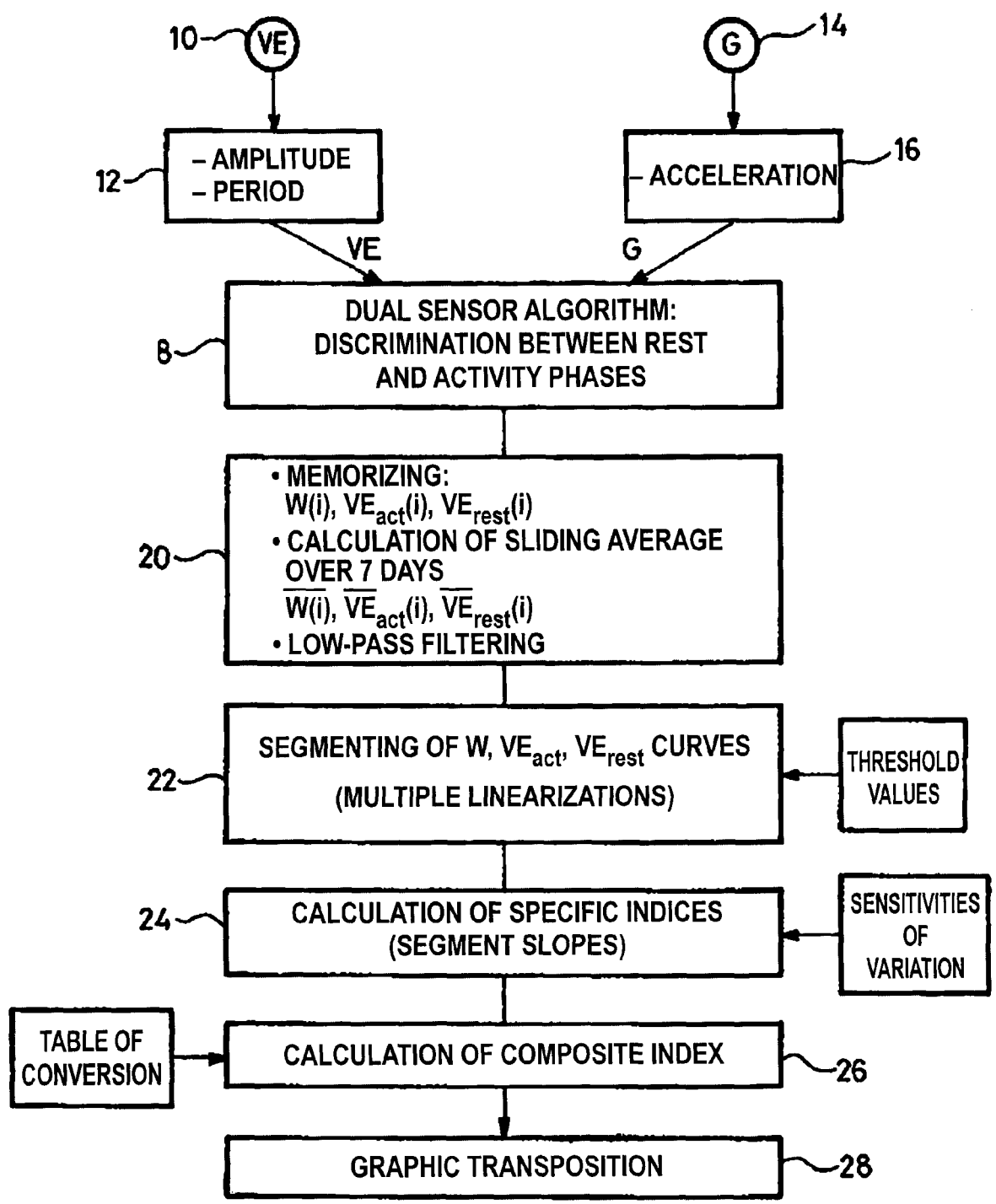
FIG_1

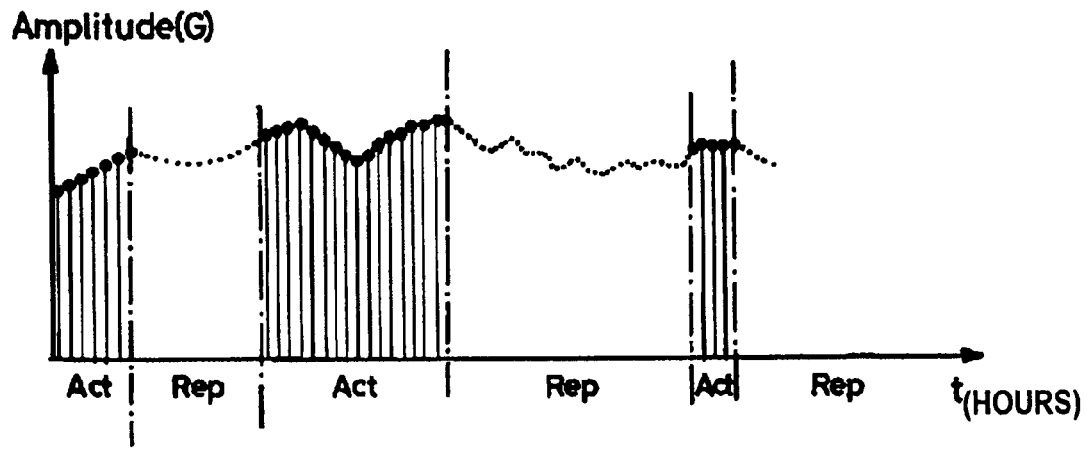
FIG_2
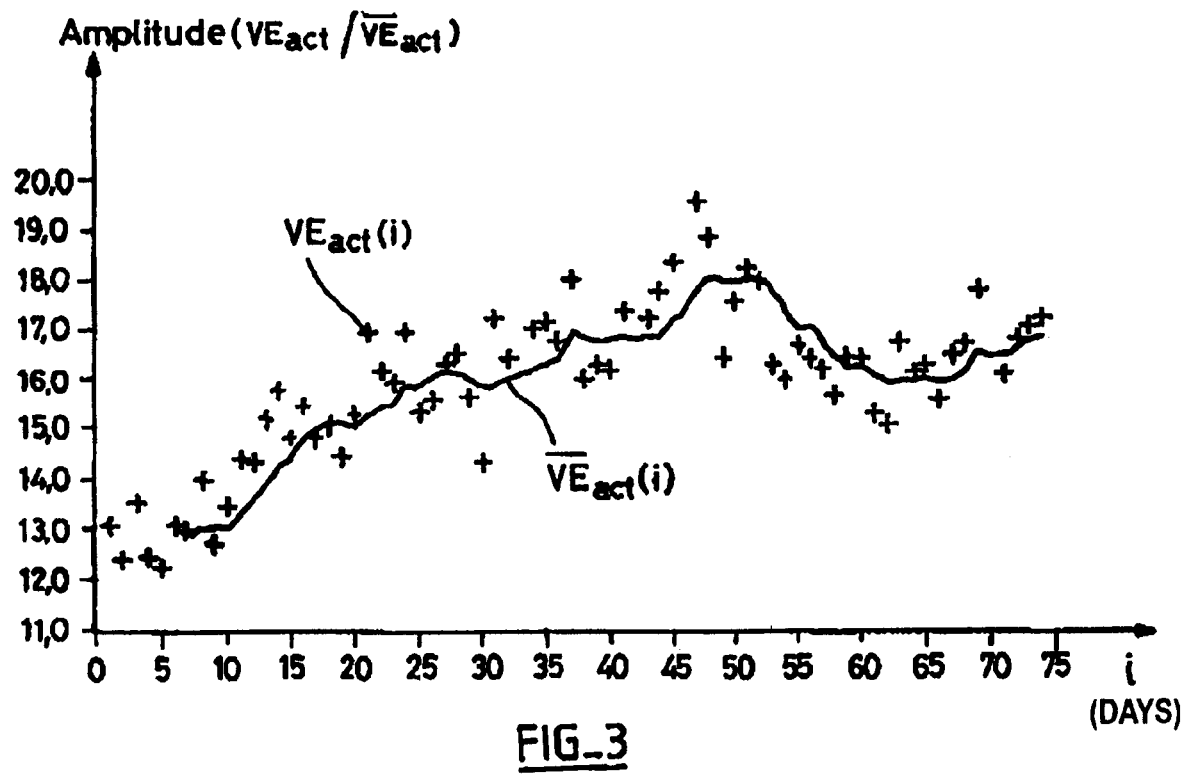
FIG_3

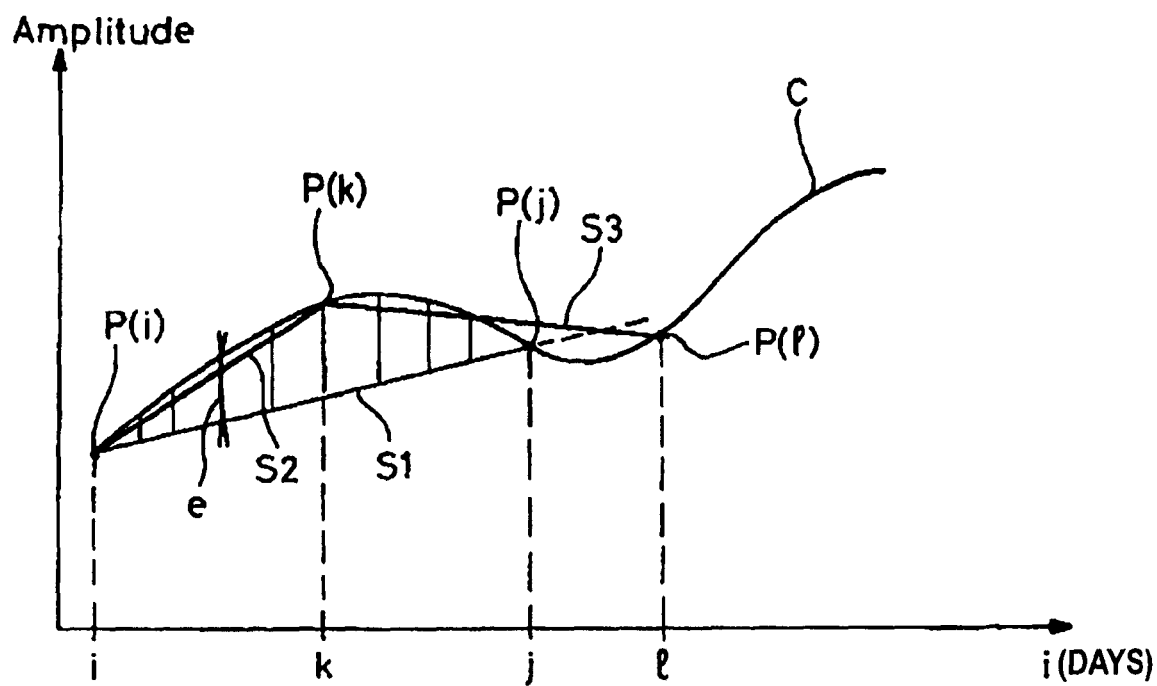
FIG_4
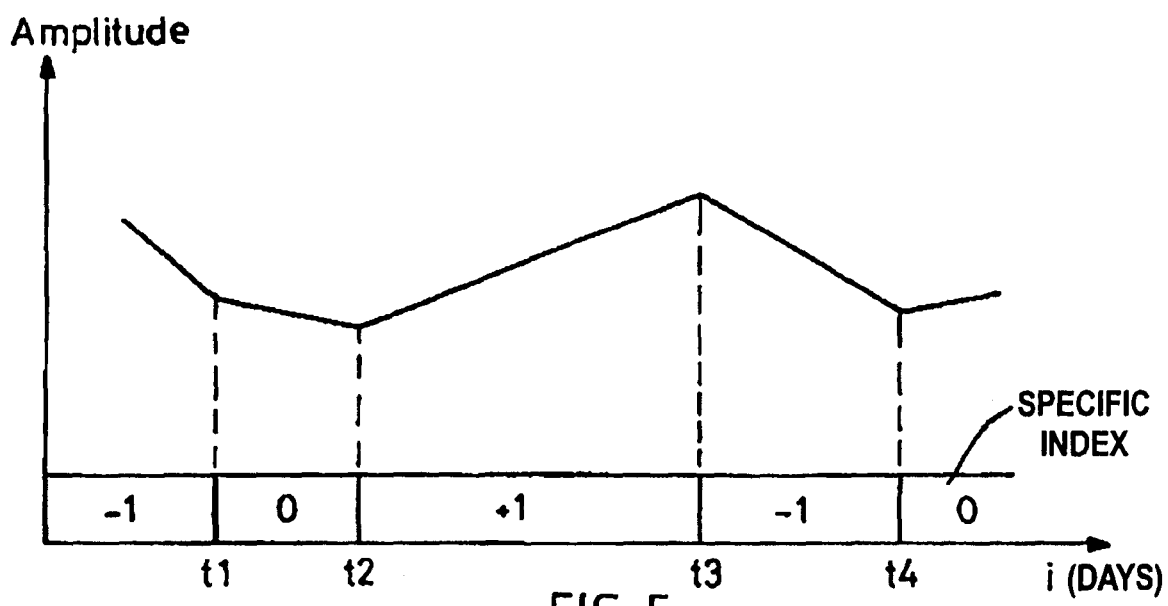
FIG_5

| | | VE$_{rest}$ INDEX | | |
|---|---|---|---|---|
| VE$_{act}$ INDEX | W INDEX | -1 | 0 | +1 |
| -1 | -1 | +1 | 0 | -2 |
| | 0 | +2 | +1 | -1 |
| | +1 | +2 | +1 | 0 |
| 0 | -1 | +1 | 0 | -2 |
| | 0 | +1 | 0 | -1 |
| | +1 | +2 | +1 | 0 |
| +1 | -1 | 0 | -1 | -2 |
| | 0 | 0 | -1 | -2 |
| | +1 | +1 | 0 | -1 |
FIG_6
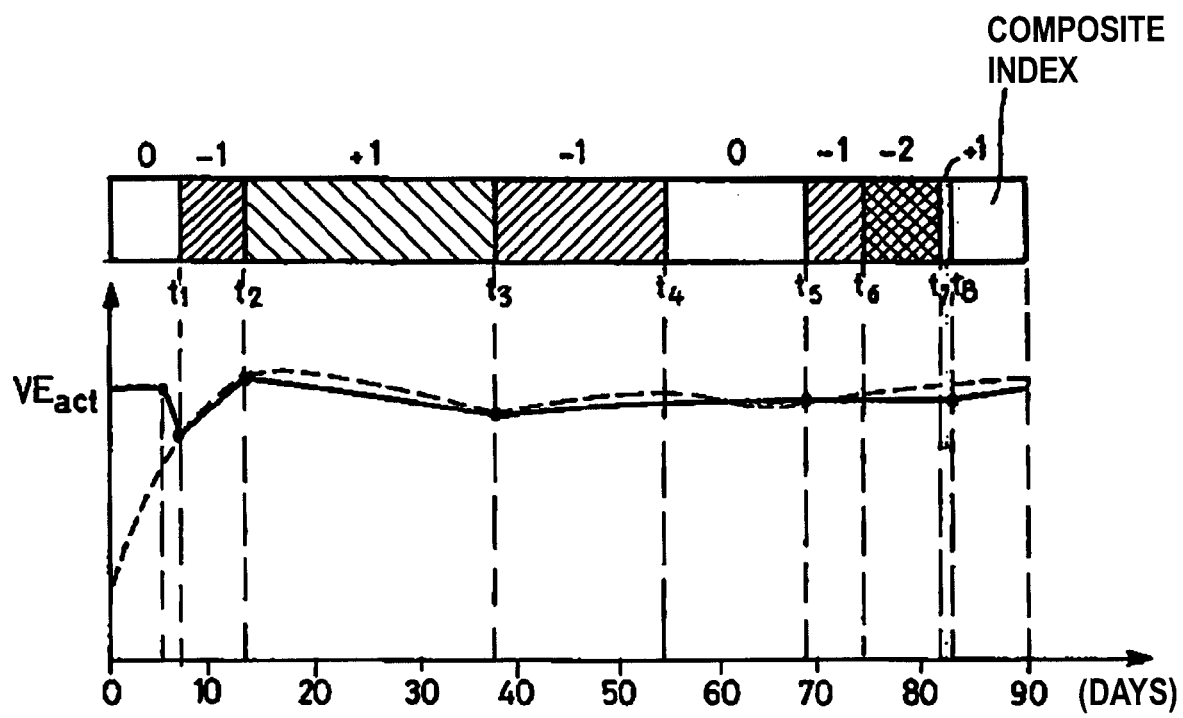
FIG_7

ACTIVE IMPLANTABLE MEDICAL DEVICES, NOTABLY FOR PACING, RESYNCHRONIZATION, DEFIBRILLATION AND/OR CARDIOVERSION, HAVING IMPROVED DIAGNOSIS OF THE PATIENT'S CLINICAL STATUS

FIELD OF THE INVENTION

The present invention relates to "active implantable medical devices" as such devices are defined by the Jun. 20, 1990 Directive 90/385/CEE of the Counsel of the European Community, and more particularly to cardiac pacemakers, resynchronization, cardioverters and/or defibrillators intended to treat cardiac rhythm disorders, and to active implantable medical devices intended to diagnosis cardiac rhythm disorders. The invention more particularly concerns, among such devices, those referred to as "multisite" devices, for which the electrodes are placed in a plurality of respective distinct sites in the heart including two ventricular sites, left and right, and at least one atrial site. Multisite devices can be "triple chamber" devices (dual ventricular pacing and right atrial pacing/sensing) or "quadruple chamber" devices (dual ventricular pacing and dual atrial pacing/sensing). The invention is even more particularly related to such devices whose operation is enslaved (i.e., responsive) to parameters collected (sensed) by sensors that allow for assessing metabolic needs and/or the current activity level of the patient.

BACKGROUND OF THE INVENTION

Enslaved active implantable medical devices (sometimes such pacing devices are known as rate responsive devices in the context that an applied cardiac pacing rate is adjusted according to the parameters collected) generally employ two different kinds of sensors, i.e. one sensor for the measurement of a corporal parameter predominantly physiologic in nature, and one sensor for the measurement of a corporal parameter predominantly physical in nature.

For purposes of illustration, a particular example of a minute-ventilation (VE) sensor will be used as the physiologic sensor, corresponding to a conventional practice. However, it should be understood that this example is not intended to limit the scope of the invention, and other types of sensors may equally be used to obtain a physiologic parameter other than minute ventilation, which devices provide a signal that is representative of the patient's metabolic needs (for example, a sensor that measures blood oxygen saturation) or hemodynamic status (for example, an intracardiac bioimpedance sensor). The term "sensor" should be understood to include the physical components that interface with the patient to collect the information underlying the patient parameter and the related electronic circuits, algorithms and logic that process the collected information to produce a parameter measurement.

Similarly, for purposes of illustration a particular example of an acceleration (G) sensor will be used as the physical parameter (activity), corresponding to a conventional practice. Here, too, other types of physical sensors can be considered, notably to detect the patient's movements. Generally, the physical (activity) sensor is characterized by having a shorter response time than the physiological sensor, in order to allow a very fast detection of short-duration activity, and to use that detected activity before a change in the patient's metabolic demand can be identified through a significant change of the collected physiological parameter, which varies more slowly.

European patent EP 0,750,920, and its counterpart U.S. Pat. No. 5,722,996, commonly assigned herewith to ELA Medical, describe such an active implantable medical device that is enslaved to two sensors, operating a selection of one or the other sensor as the control parameter so as to take into account only that which gives the more relevant signal at a given moment. European patent EP 0,919,255 and its counterpart U.S. Pat. No. 6,336,048, also commonly assigned herewith to ELA Medical, describe an enslavement that is based upon the use of a combination of the signals provided by these two sensors.

Many patients implanted with an active implantable medical device present a normal atrio-ventricular conduction (i.e., each atrial event is followed by an associated ventricular depolarization) and therefore have no standard indication for being implanted with a pacemaker. A multisite device is then indicated, so as to treat the indicated heart failure, in order to improve the general hemodynamic state of these patients, through permanent jointly pacing of right and left ventricles so that they can be resynchronized. Such therapy has often provided surprisingly effective results on patients suffering from Class III heart failure, that were not improved through the prior known, classical treatments. European patent EP-A-1,543,864 and its U.S. counterpart published patent application US 2005/0,131,471 (commonly assigned herewith to ELA Medical) describe such a multisite device.

The starting point of the present invention lies in the observation by the inventor that medical practitioners have no convenient tool that allows them, during routine visits, to immediately and objectively assess whether the applied therapy actually led to an expected improvement of the patient's exercise performance status. Therefore, there is a recognized need to have such a function implemented in such devices that permits the elaboration and memorization of the information relating to the evolution of the patient's clinical status between two routine visits to the medical practitioner, that is over a long period of time, for these visits are usually spaced several months apart.

An objective assessment of this evolution will notably allow the practitioner to determine whether multisite pacing is beneficial, and eventually to choose a programming that is more appropriate to the particular patient, or, for example, to be informed about the occurrence of important ventilation disorders, not diagnosed by the patient himself.

Heretofore, for the purpose of evaluating, for example, the effect of a particular programming on the patient's status between two routine visits, the practitioner could only rely on the facts and feelings reported by the patient—such information being subject to a strong subjectivity—or on clinical tests performed or prescribed—the latter information provided by such tests only reflecting the patient's status at the time of the tests, with no retrospective overview on the improvement or degradation of the patient's status between visits.

There also is an existing need for providing a synthetic and significant diagnostic aid that can be represented through a simple and clear symbolic form, i.e. a clear visual presentation, to the practitioner during routine visits.

OBJECTS AND SUMMARY OF THE INVENTION

It is, therefore, an object of the present invention to propose an improved device of the type referred to above, i.e. a device of the multisite type comprising two sensors, one physiologic and one physical, that is further able to analyze and memorize the information provided by these two sensors between two practitioner visits, spaced several months apart, so as to provide to the practitioner, when the moment comes, help to diagnose information representative of the evolution of the patient's clinical status, more preferably the exercise performance status, since a preceding visit.

Broadly, the present invention is directed to an improved device of the dual sensor type, such as the devices described in the patents referred to above, that is a device comprising: means for measuring a corporal parameter that is predominantly physiologic and providing a physiologic signal, preferably the minute ventilation; means for measuring a corporal parameter predominantly physical and providing a physical signal, preferably the acceleration; means for discriminating between rest and activity phases of this patient, operating in response to said physiologic and physical signals, and providing an indication of the patient's status; and means for analysis, in order to process and combine the physical signals, the physiologic signals, and the status indicator, and memorizing the obtained results in the format of a data history.

In a manner characteristic of the invention, the analysis means preferably comprises: first means for establishing characteristics providing, for successive dates, values that are representative of, over a given duration: (1) the physical signal during activity phases of the patient, (2) the physiologic signal during the patient's activity phases, and/or (3) the physiologic signal during patient's rest phases; second means, to search for a plurality of remarkable dates for each of the characteristics thus obtained; third means, to allocate specific indices of clinical status respectively to each of the periods of time between said remarkable dates for each of the characteristic thus obtained; and fourth means, to combine into a composite index the specific indices this determined.

In a preferred embodiment, the second means advantageously comprises means for performing a multiple linearization, to transform the characteristic in a continuous series of line segments, notably segments whose endpoints are points of the characteristic, each segment end defining one of the remarkable dates for the associated characteristic. As used herein, the term "remarkable dates" are used to define segments of the curve that present a stable condition, for example a constant slope (the first derivative), where the value of the curve characteristic P is relatively constant between two remarkable dates, in a zone of homogeneous values P(r), i<r<j. The definition of these remarkable dates is done by choosing threshold values in the iterative method, the characteristic dates separate segments that cannot be converted on a single linearization without losing large variations in slope or magnitude. It is the period between the two dates which is important, not the remarkable dates themselves.

The means for linearization may be an iterative means, operating through application of a regression formula, notably defining a remarkable date if the sum of the absolute values of the deviations between the segment and the characteristic exceeds a first predetermined threshold value, and only if each of these deviations between the segment and the characteristic dos not exceed a second predetermined threshold value.

In a preferred embodiment, the third means advantageously comprises means for evaluating the slope of the line segments and allocating a corresponding specific index as a function of the slope value.

Preferably, the fourth means advantageously comprises means implementing a pre-recorded truth table univalently providing, for each possible combination of specific indices, a corresponding value of composite index.

In a preferred embodiment, the first means for establishing characteristics preferably establishes the characteristics based upon moving averages of the values of the physical signal accumulated over the activity phases, of the physiologic signal over the activity phases, and/or of the physiologic signal over rest phases.

The specific indices and composite indices of clinical status are typically reevaluated on a daily basis.

BRIEF DESCRIPTION OF THE DRAWINGS

Further benefits, features and characteristics of the present invention will become apparent to a person of ordinary skill in the art in view of the following detailed description of the invention, made with in reference to the annexed drawings, in which:

FIG. 1 is a block schematic of a process flow chart illustrating different functions of a device in accordance with a preferred embodiment of the invention, that are implied in the determination of the indices representative of the evolution of the patient's clinical parameters;

FIG. 2 is a plot of the amplitude variations of an acceleration signal G acquired over time, taken into account by the device of the present invention;

FIG. 3 is a plot of the amplitude variations of an average minute ventilation measurement MV during activity, acquired over a period of several weeks, taken into account by the device of the present invention;

FIG. 4 is a plot illustrating a representative segmenting of a characteristic through multiple linearizations;

FIG. 5 is a plot illustrating the allocation of the values of the index specific to the segmented characteristic;

FIG. 6 is a truth table providing the composite index as a function of the values taken by the various specific indices; and FIG. 7 shows a diagrammatic representation of the variations of the composite index over time, in a manner immediately comprehensible by the practitioner.

DETAILED DESCRIPTION OF THE INVENTION

One will now describe a preferred embodiment of the invention with reference to the drawings FIGS. 1-7. The present invention can be preferably implemented by an appropriate programming of the software of a known enslaved pacemaker. Suitable devices include those implantable devices marketed by ELA Medical, Montrouge, France, such as the *Symphony and ELA Rhapsody* brand pacemakers. These and other similar devices are equipped with programmable microprocessors and memory, including circuits intended to acquire, format and process electrical signals collected by implanted electrodes and various sensors and store (memorize) such signals and data. It is also possible to upload towards these devices, by telemetry, pieces of software that will be stored in internal memory and run so as to implement the features of the invention, described in more detail below. Implementing the features and functionality of the invention into these devices is believed to be within the abilities of a person of ordinary skill in the art, subject to the variations of implementation that such persons may employ, and will therefore not be described in detail in this document.

With reference to FIG. 1, a device according to a preferred embodiment of the present invention includes a sensor 10 (characterized as a minute ventilation sensor (ve) providing a signal representative of the patient's metabolic needs, typically a transthoracic impedance signal. An analysis of the periodic variations (amplitudes and successive periods) is performed by stage 12, which provides a minute ventilation measurement signal (VE). The device also includes a physical sensor that detects the patient's movements, typically an acceleration (g) sensor 14 associated to a sampling circuit 16 that provides a succession of digitized samples, having a sampling step of 125 ms, for instance, providing an acceleration signal (G).

Based upon the information VE and G concurrently provided, the device is thus operating an enslavement of the "dual sensor" type as described in European patent EP 0,750,920 and its counterpart U.S. Pat. No. 5,722,996, and European patent EP 0,919,255 and its counterpart U.S. Pat. No. 6,336,048 cited above, which patents are incorporated herein by reference in their entirety, and more preferably provides an enslavement of the pacing rate and eventual adaptation of operating parameters. That enslavement function as such is not part of the present invention though, and will therefore not be described further into details.

Nevertheless, the enslavement algorithm has the advantage to provide a function of discrimination between a patient's activity and rest phases (stage 18) based upon the instantaneous information delivered by ve and g sensors 10 and 14, resulting in a status index able to take at least two values: "activity" ("act") and "rest" ("rest"). It should be understood that other values are also possible, for example: "recovery after exercise," which will be assimilated to an activity phase, or "sleep" which is a particular case of rest phase.

For the implementation of the invention, the device is collecting, in a distinct manner for activity phases and rest phases, the data provided by the ve and g sensors 10 and 14, and is memorizing, based on said data:

the sum W(i) of the measurement of sensor signal G in activity phase, the average minute ventilation VEact(i) during activity phases, measured over the last 24 hours, and the average minute ventilation VErest(i) during rest phases, measured over the last 24 hours.

FIG. 2 shows more precisely the way W(i) is obtained and updated, that datum being representative of the cumulative effort developed by the patient over the last 24 hours: as said above, the sensor g is providing a series of digitized samples G, for example, with sampling intervals of 125 ms, the variation of which over time is illustrated on FIG. 2. Also, the status indicator allows to distinguish activity phases (Act) and rest phases (Rest). The device operates a summing of the values of the samples acquired over the last 24 hours, but inhibiting said summing during rest phases, and therefore only summing values corresponding to periods of activity.

The parameter VEact(i) is an average value of minute ventilation VE during activity phases. The parameter VErest(i) is an average value of minute ventilation VE during rest phases. For these two parameters, the obtained average is weighted by dividing it by the duration spend in activity or rest phases, respectively.

Typically, these various parameters: W(i), VEact(i) and VErest(i) are evaluated and memorized on a periodic basis, preferably a daily basis, from the first day i=1 following the implantation of the device or the last visit with the practitioner, until a duration that can typically reach around i=90 days, in the case of quarterly routine visits.

Based upon the raw values W(i), VEact(i) and VErest(i) thus determined and memorized, the device then calculates (stage 20) a moving average over 7 days W(i)/, VEact(i)/, VErest(i)/. Advantageously, these averages are also subjected to a low-pass filtering of $2^{nd}$ order (or any other smoothing algorithm of the low-pass type), in order to smooth rough variations thereof, and to let only the slowest evolutions appear. The slowest evolutions are the variations that are believed to be significant from a long-term viewpoint.

FIG. 3 shows as a representative example, the variations of the parameter VEact(i) over time for a duration of several weeks. The crosses show the values VEact(i) calculated daily, the full line representing the moving average VEact(i) over seven days, also calculated daily.

The following step (stage 22), characteristic of the invention, is a segmenting step, which models each of the three curves W(i)/, VEact(i)/ and VErest(i)/ in the form of a continuous succession of line segments whose endpoints are points of the curve under consideration. The modeling is preferably performed by an application of the method of multiple linearizations as described below, with reference to FIG. 4. Starting from an initial point P(i) located at an abscissa i (i≧7, the averages of the very first days being not significant), one considers a point P(j) at an abscissa j (j>i). That point defines on curve C a chord P(i)P(j), that is: a segment S1. One then applies a regression formula consisting of calculating, for all points on curve C between P(i) and P(j), the sum of the absolute values of the successive variances e between curve C and segment S1. One then increases j, i.e., one is moving point P(j) towards the straight line, until the sum calculated based upon the regression formula reaches a first given threshold value (the first threshold value proper to each of the three curves, is predetermined or programmable and has been previously evaluated based upon results of clinical studies).

The threshold value cannot be "defined" as standard value, because the aim of this threshold is to be adapted by the physician-practitioner when looking the result of linearization. For each period of follow-up (and also each patient) the same threshold may "divide" a curve onto various number of segments. The threshold therefore may be considered as a "zoom" value. For example, given a curve over n days, there is a threshold value A, which converts the curve onto 1 single segment, and a value B (B<<A) for which the curve will be converted into n different segments. A threshold value between A and B then will convert the curve into multiple lines, between 1 and n, corresponding to more or less "precision" according to the selected threshold. It has been found that if you have changes in the slope of more than 5 to 10%, it defines a new period for ventilation, and similarly for activity sensor a change of around 10% implies a new period. It should be understood however, that these selected thresholds are not medical or physiologic values, but rather only mathematic values useful to linearize the curves.

As soon as one finds a value j for which the threshold is exceeded, one considers that the corresponding point P(j) in principle accounts for the second endpoint of the segment, said segment covering the period [i, j].

However, one additional criterion is applied, by operating an additional verification for all successive points comprised between P(i) and P(j): if the distance between the segment P(i)P(j) and curve C is, for one given point, higher than a second predetermined threshold, then one replaces P(j) by that new point P(k). The considered segment then becomes the segment P(i)P(k), instead of segment P(i)P(j). In other words, if for a given point P(k) the variance between the curve and the initial segment (resulting from the application of the regression formula) is higher than a given limit, then one will use as the new point, that corresponding to the maximal variance.

Indeed, the purpose of the segmenting operation is to let "remarkable dates" appear, corresponding to junction points of successive segments, and avoid an excessive smoothing of the curve that would tend to eliminate such remarkable dates.

Thus, on FIG. 4, segment S1 initially considered, is replaced by segment S2, thereby revealing the date k, corresponding to point P(k), as a remarkable date, meaning it has an unusual characteristic (it has a value that is too different from the linearization; the "error" done by linearization S1 is too large compared as the real curve) as compared to the evolution of the measurement.

The segmentation algorithm is then reiterated until the end of the curve: the point P(k) is in turn used as a starting point for the algorithm, which searches for a segment S3 between P(k) and a point P(l) likely to fulfill the criteria described above, and so on.

At the end of the process, one obtains for each of the three curves W(i)/, VEact(i)/ and VErest(i)/ a series of successive segments, joined to each other around successive remarkable dates. FIG. 5 illustrates a representative shape of a portion of such a characteristic after segmenting.

The following step (stage 24) calculates, for each of the three segmented curves and for each of the periods between two remarkable dates, an index hereinafter referred to as "specific index". The specific index is preferably determined based upon the slopes of successive line segments, by comparing each slope value to two limit values, positive and negative, referred to as "variation sensitivity". If the slope is comprised between these two values, it is considered as stable, and the index "0" is allocated to corresponding segment. Otherwise, one allocates an index '+1' or '−1' if the slope is positive or negative respectively.

FIG. 5 shows as an example, the variations of the specific index for the series of segments of the curve. In other words, after defining a certain number of remarkable dates t1, t2, t3, t4, . . . through segmenting, one determines an index that reflects the variation of the parameter under consideration, between two successive remarkable dates: low or no variation (specific index='0'), weighty increase (specific index='+1') or weighty decrease (specific index='−1'). These data are obtained for each of the three parameters W, VEact and VErest, but with remarkable dates that are not necessarily the same for each of them.

The following step (stage 26) determines a synthetic index, hereinafter referred to as "composite index", based upon various specific indices and remarkable dates. The composite index is determined based upon a truth table combining all possible values of the three specific indices determined above. This truth table, of which an example is given in FIG. 6, is established as a function of medical advices and results of clinical studies, and is supposed to reflect the relative weight of the various parameters when they are combined with each other. The truth table allocates, for each day, a value '−2', '−1', '0', '+1 or '+2' to the composite index. The value allocated is therefore likely to change every time a remarkable date has been detected for one of the three parameters W, VEact and VErest.

Advantageously, changes to the composite index are transposed into a graphical format (stage 28), through a step that can be executed by the programmer of the practitioner in charge of visiting the patient, once the programmer has retrieved from the device memory, the data to be displayed. FIG. 7, as an example, shows such a graphical display, that can be preferably presented in the form of a colored bar with different colors that are function of the index, for instance: dark green→light green→white→yellow→red for the respective values of the index +2, +1, 0, −1, −2. The graphical code is advantageously displayed on a screen simultaneously with each, or only one, of the three curves W(i)/, VEact(i)/ and VErest(i)/ as shown on FIG. 7.

The graphical display allows the practitioner, for example, to immediately identify a period of general degradation (in red), determine the remarkable dates corresponding to that evolution, and eventually perform a more precise diagnosis by examining the variations of W, VEact and VErest and/or other parameters memorized by the device during the period under consideration. For example, on FIG. 7, one can see that the episode of aggravation comprised between t1 and t2 is very probably related to the factor VEact (t1 and t2 are remarkable dates for only VEact), whereas the episode of serious aggravation comprised between t6 and t7 is not related to this factor (t6 and t7 are not remarkable dates for VEact), but probably to variations of the other factors, not shown on this drawing.

Hence the practitioner will immediately recognize, for the period under consideration, precise time marks that will help in formulating a diagnosis and in interrogating the patient.

One skilled in the art will appreciate that the present invention can be practiced by other than the described embodiments, which are presented for purposes of illustration and not of limitation.

I claim:

1. An active implantable medical device for pacing, resynchronization, defibrillation and/or cardioversion, or an active implant intended to diagnose a cardiac rhythm disorder, comprising:

means for measuring a predominantly physiologic corporeal parameter and providing a physiologic signal representative thereof;

means for measuring a predominantly physical corporeal parameter and providing a physical signal representative thereof;

means for discriminating a patient status of a patient between rest phases and activity phases, operating in response to said physiologic signal and said physical signal, means for providing a status index corresponding to the patient status;

memory for memorizing the physiologic signal, the physical signal and the status index; and means for analyzing the patient status, responsive to the physiologic signal, the physical signal and the status index, wherein said means for analysis comprises:

first means for providing characteristic values as a function of time for the physical signal during the activity phases of the patient, the physiologic signal during the activity phases of the patient and/or the physiologic signal during the rest phases of the patient, second means for determining a plurality of remarkable dates from the characteristic values, the plurality of remarkable dates defining endpoints of a plurality of characteristic periods and time period between two successive remarkable dates defining a characteristic period of the plurality of characteristic periods, third means for allocating a specific index of specific indices of the patient status respectively to each characteristic period of the plurality of characteristic periods, wherein the specific index is a numerical value indicating improvement, degradation, or stability of the patient status of each characteristic period with respect to the patient status of the immediately preceding characteristic period, and fourth means for combining one or more said specific indices into a composite index.

2. The device of claim 1, wherein said second means further comprises means for performing a multiple linearization, said means for performing a multiple linearization transforms each characteristic value of said characteristic values into a continuous series of line segments, each line segment of said line segments having a pair of endpoints and a slope, said pair of endpoints representing one of said plurality of remarkable dates.

3. The device of claim 2, wherein each line segment of the continuous series of line segments defines each characteristic period of the characteristic periods.

4. The device of claim 2, wherein said means for performing a multiple linearization iteratively operates through an application of a regression formula.

5. The device of claim 4, wherein said means for performing a multiple linearization calculates absolute values of the variance between said continuous series of line segments and said characteristic values and defines a remarkable date of said plurality of remarkable dates if the sum of the absolute values of the variance is greater than a first predetermined threshold value.

6. The device of claim 5, wherein said means for performing a multiple linearization defines said remarkable date of said plurality of remarkable dates only if each of the absolute values of the variance between said continuous series of line segments and said characteristic values is less than a second predetermined threshold.

7. The device of claim 2, wherein said third means evaluates the slope of said line segments and allocates the corresponding specific index as a function of said slope.

8. The device of claim 1, wherein said fourth means implements a prerecorded truth table providing, for each possible combination of said specific indices, a corresponding value of said composite index.

9. The device of claim 1, wherein said first means calculates moving averages of said physical signal during said activity phases and establishes characteristic values based upon the calculated moving averages.

10. The device of claim 1, wherein said first means calculates moving averages of said physiologic signal during said activity phases and establishes characteristic values based upon the calculated moving averages.

11. The device of claim 1, wherein said first means calculates moving averages of said physiologic signal during said rest phases and establishes characteristic values based upon the calculated moving averages.

12. The device of claim 1, wherein said specific indices and said composite index are periodically re-evaluated.

\* \* \* \* \*